(12) United States Patent
Corbitt, Jr. et al.

(10) Patent No.: US 9,943,706 B2
(45) Date of Patent: Apr. 17, 2018

(54) TARGETING IMPLANT FOR EXTERNAL BEAM RADIATION

(71) Applicant: Surgical Radiation Products, LLC, Lake Worth, FL (US)

(72) Inventors: John D. Corbitt, Jr., Palm Beach Gardens, FL (US); Lori Anthony, Lake Worth, FL (US); Kishore Kumar Dass, Jupiter, FL (US); Jay Sussman, Lake Worth, FL (US)

(73) Assignee: SURGICAL RADIATION PRODUCTS, LLC, Lake Worth, FL (US)

( * ) Notice: Subject to any disclaimer, the term of this patent is extended or adjusted under 35 U.S.C. 154(b) by 23 days.

(21) Appl. No.: 15/190,615

(22) Filed: Jun. 23, 2016

(65) Prior Publication Data

US 2016/0296765 A1    Oct. 13, 2016

Related U.S. Application Data

(60) Continuation-in-part of application No. 15/078,068, filed on Mar. 23, 2016, which is a division of
(Continued)

(51) Int. Cl.
*A61N 5/10* (2006.01)
*A61B 17/34* (2006.01)
(Continued)

(52) U.S. Cl.
CPC ............ *A61N 5/1049* (2013.01); *A61B 17/06* (2013.01); *A61B 17/06166* (2013.01);
(Continued)

(58) Field of Classification Search
CPC ..... A61B 6/12; A61B 17/06; A61B 17/06166; A61B 17/3468; A61B 2090/3983;
(Continued)

(56) References Cited

U.S. PATENT DOCUMENTS 3,185,299 A   5/1965   Trainer
3,194,239 A   7/1965   Sullivan
(Continued)

FOREIGN PATENT DOCUMENTS

RU       2145187        2/2000
WO    WO2002070167      9/2002
(Continued)

OTHER PUBLICATIONS

Celine Bourgier, et al., Early Side Effects of Three-Dimensional Conformal External Beam Accelerated Partial Breast Irradiation to a Total Dose of 40 GY in One Week (A Phase II Trial), Int. J. Radiation Oncology Biol. Phys., vol. 31, No. 5, pp. 1228-1235, 2011.
(Continued)

*Primary Examiner* — Christine H Matthews
*Assistant Examiner* — Joshua D Lannu
(74) *Attorney, Agent, or Firm* — Steven M. Greenberg, Esq.; CRGO Law

(57) ABSTRACT

A radiation target is provided. The radiation target includes an implant, which includes a marker comprising a channel defined therethrough from one end of the marker to an opposite end of the marker. The implant further comprises a single non-looping suture thread disposed within the channel and a coating applied to both the single non-looping suture thread and to the marker.

13 Claims, 18 Drawing Sheets

Related U.S. Application Data application No. 13/348,965, filed on Jan. 12, 2012, now Pat. No. 9,320,517.

(51) Int. Cl.

| | |
|---|---|
| *A61B 17/06* | (2006.01) |
| *A61B 90/00* | (2016.01) |
| *A61B 17/00* | (2006.01) |
| *A61B 6/12* | (2006.01) |
| *A61B 8/08* | (2006.01) |
| *A61F 2/12* | (2006.01) |

(52) U.S. Cl.
CPC ............ *A61B 17/3468* (2013.01); *A61B 6/12* (2013.01); *A61B 8/0841* (2013.01); *A61B 2017/00004* (2013.01); *A61B 2017/0088* (2013.01); *A61B 2017/3413* (2013.01); *A61B 2090/3908* (2016.02); *A61B 2090/3966* (2016.02); *A61B 2090/3983* (2016.02); *A61B 2090/3987* (2016.02); *A61F 2/12* (2013.01); *A61N 2005/1061* (2013.01)

(58) Field of Classification Search
CPC .. A61B 2090/3987; A61B 2017/00004; A61B 2090/3966; A61B 2017/0088; A61B 2017/3413; A61B 2090/3908; A61B 8/084; A61F 2/12; A61N 5/1049; A61N 2005/1061

See application file for complete search history.

(56) References Cited

U.S. PATENT DOCUMENTS

| | | | |
|---|---|---|---|
| 5,047,050 A | 9/1991 | Arpesani | |
| 5,628,780 A | 5/1997 | Helland et al. | |
| 5,951,590 A | 9/1999 | Goldfarb | |
| 6,007,475 A | 12/1999 | Slater et al. | |
| 6,026,818 A * | 2/2000 | Blair ................... | A61F 13/44 128/899 |
| 6,200,258 B1 | 3/2001 | Slater et al. | |
| 6,371,904 B1 | 4/2002 | Sirimanne et al. | |
| 6,426,145 B1 | 7/2002 | Moroni | |
| 6,635,082 B1 | 10/2003 | Hossainy et al. | |
| 6,666,811 B1 | 12/2003 | Good | |
| 6,746,465 B2 | 6/2004 | Diederich et al. | |
| 6,821,283 B2 | 11/2004 | Barzell et al. | |
| 7,041,047 B2 | 5/2006 | Gellman et al. | |
| 7,127,040 B2 | 10/2006 | Sayre et al. | |
| 7,229,417 B2 | 6/2007 | Foerster et al. | |
| 7,407,476 B2 | 8/2008 | Lubock et al. | |
| 7,497,819 B2 | 3/2009 | White et al. | |
| 7,524,274 B2 | 4/2009 | Patrick et al. | |
| 7,776,310 B2 | 8/2010 | Kaplan | |
| 7,783,336 B2 | 8/2010 | Macfarlane et al. | |
| 7,831,293 B2 | 11/2010 | Ellis et al. | |
| 7,862,496 B2 | 1/2011 | Hermann et al. | |
| 7,862,498 B2 | 1/2011 | Nguyen et al. | |
| 7,942,843 B2 | 5/2011 | Tune et al. | |
| 7,959,900 B2 | 6/2011 | Peng | |
| 2002/0095205 A1 | 7/2002 | Edwin et al. | |
| 2002/0147382 A1* | 10/2002 | Neisz ................. | A61B 17/0401 600/29 |
| 2005/0080337 A1 | 4/2005 | Sirimanne et al. | |
| 2005/0080338 A1 | 4/2005 | Sirimanne et al. | |
| 2005/0171428 A1 | 8/2005 | Fichtinger et al. | |
| 2007/0038014 A1 | 2/2007 | Cox et al. | |
| 2007/0112385 A1* | 5/2007 | Conlon ............... | A61B 17/0401 606/232 |
| 2008/0033286 A1 | 2/2008 | Whitmore et al. | |
| 2008/0228164 A1* | 9/2008 | Nicoson ................. | A61B 90/39 604/506 |
| 2008/0234572 A1 | 9/2008 | Jones | |
| 2008/0281388 A1 | 11/2008 | Corbitt et al. | |
| 2009/0018636 A1 | 1/2009 | Gailloud et al. | |
| 2009/0087380 A1 | 4/2009 | Fasching et al. | |
| 2009/0216115 A1* | 8/2009 | Seiler ..................... | A61B 90/98 600/426 |
| 2009/0275793 A1 | 11/2009 | Black et al. | |
| 2010/0099939 A1 | 4/2010 | Sutton et al. | |
| 2010/0222672 A1 | 9/2010 | Macfarlane et al. | |
| 2011/0004094 A1 | 1/2011 | Stubbs et al. | |
| 2012/0179027 A1 | 7/2012 | Suthanthiran et al. | |

FOREIGN PATENT DOCUMENTS

| | | |
|---|---|---|
| WO | WO2007075241 | 7/2007 |
| WO | WO2010126949 | 11/2010 |
| WO | WO2011085034 | 7/2011 |

OTHER PUBLICATIONS

Tanya S. Berrang, et al., Three-Year Outcomes of a Canadian Multicenter Study of Accelerated Partial Breast Irradiation Using Conformal Radiation Therapy, Int. J. Radiation Oncology Biol. Phys., vol. 81, No. 5, pp. 1220-1227, 2011.

Fiducial Markers: Guide & Procedure Based Recommendations, CIVCO Medical Solutions, "Breast," 2012, p. 3.

Program—Radiation Therapy: Emerging Breast Treatment & RT, Winter 2009, photo caption at p. 8.

\* cited by examiner

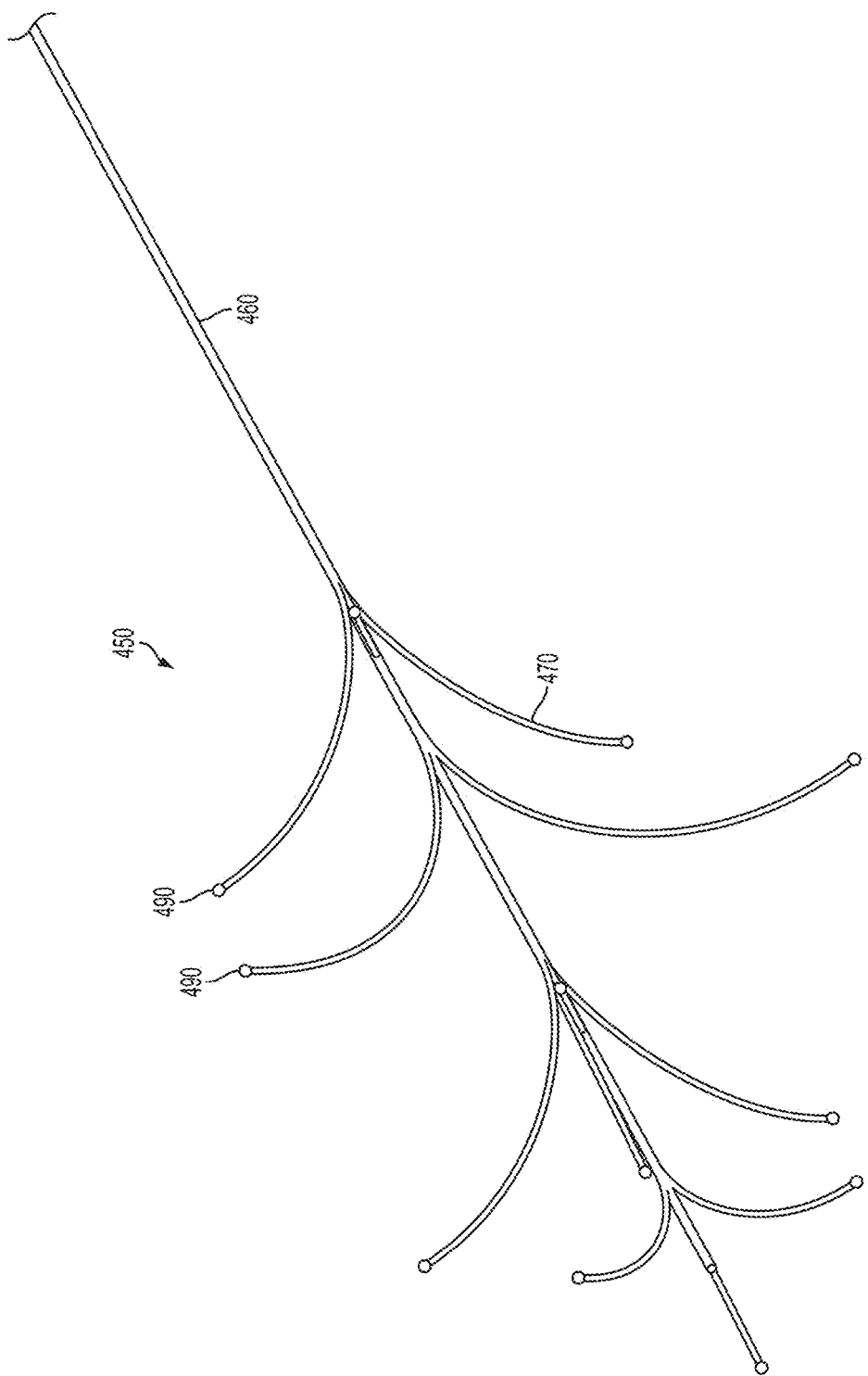

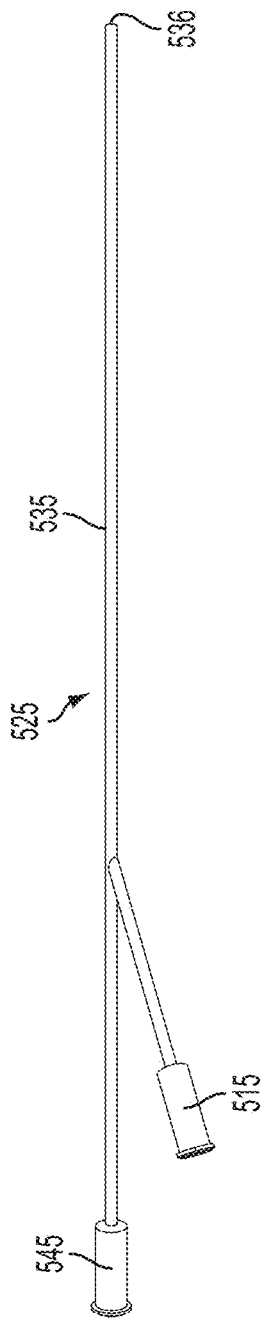

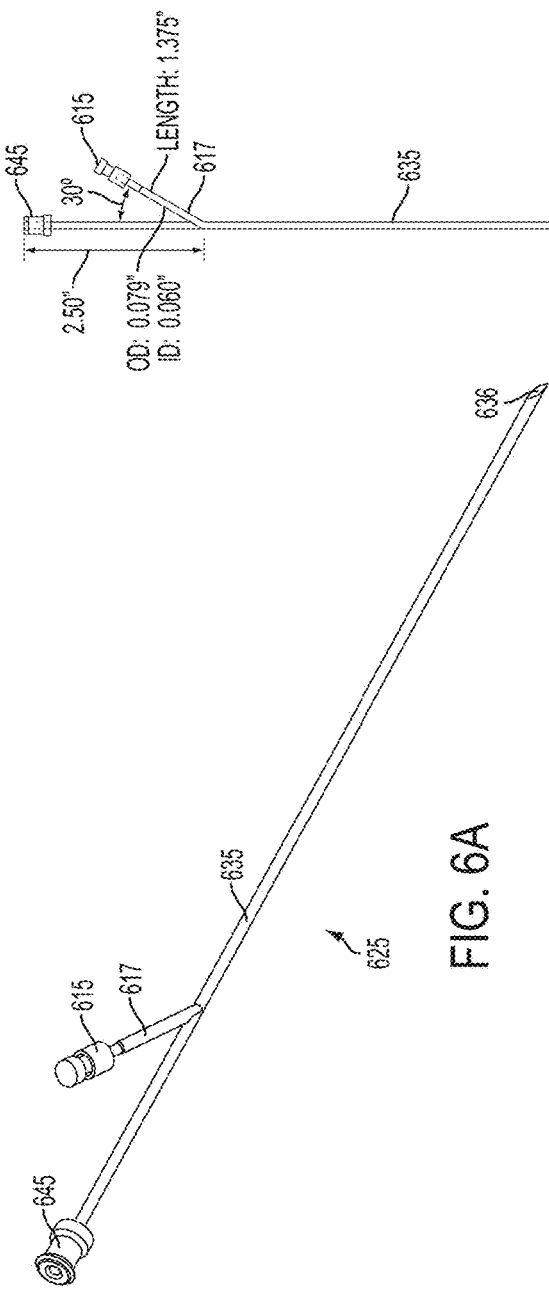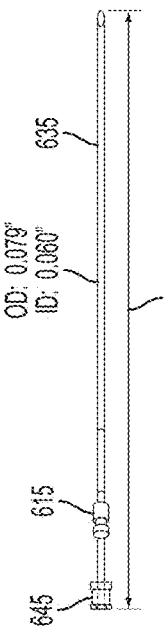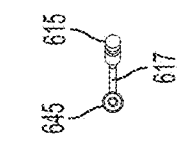

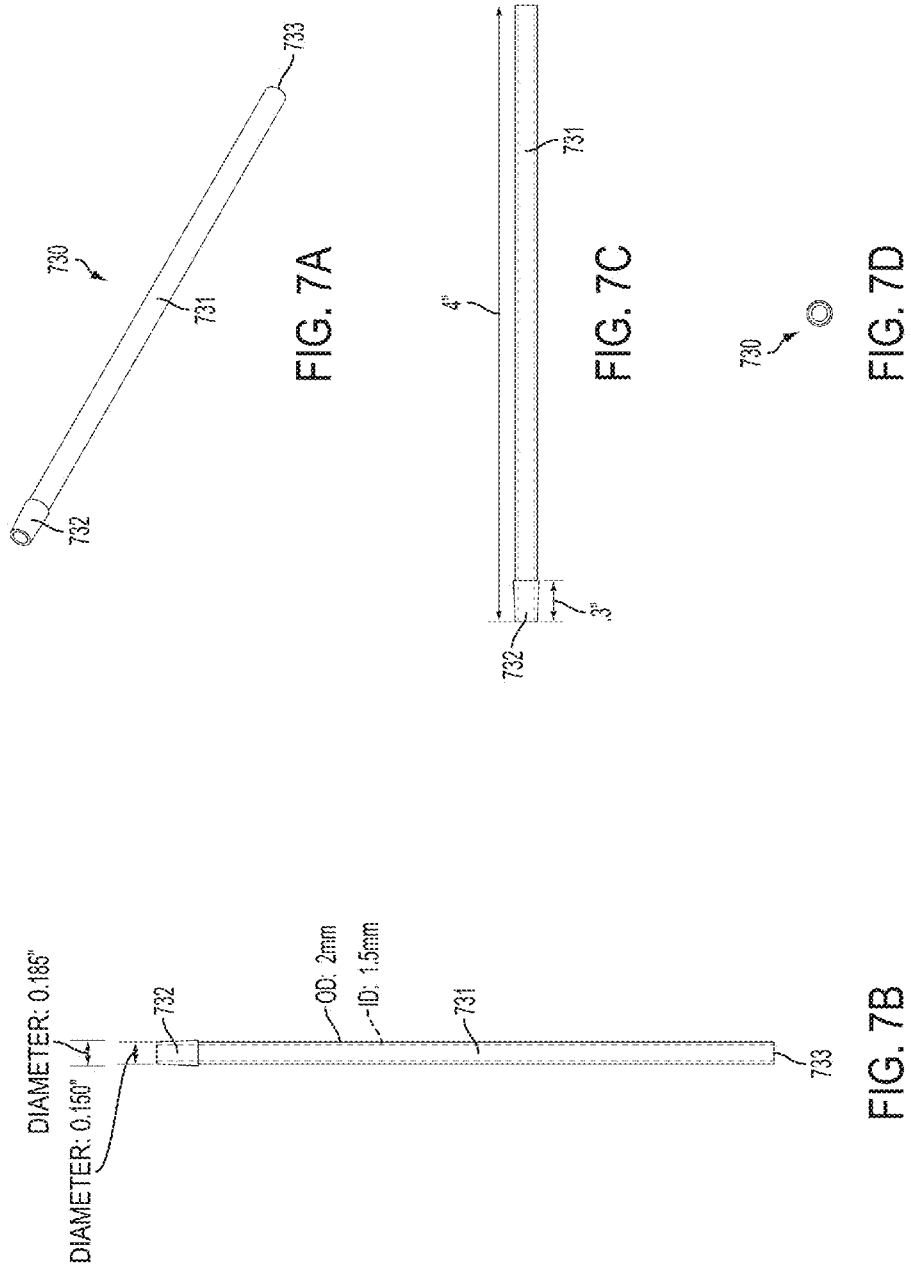

TARGETING IMPLANT FOR EXTERNAL BEAM RADIATION

CROSS-REFERENCE TO RELATED APPLICATIONS

This application is a Continuation-in-Part of U.S. patent application Ser. No. 15/078,068, filed on Mar. 23, 2016, currently pending, which is a Divisional of U.S. patent application Ser. No. 13/348,965, filed on Jan. 12, 2012, now U.S. Pat. No. 9,320,517, which are incorporated herein by reference in their entirety.

BACKGROUND OF THE INVENTION

Field of the Invention

The present invention relates to a medical device and, more particularly, to an in-vivo medical device for use during external beam radiation therapy (EBRT).

Description of the Related Art

Radiation for breast cancer is most often accomplished by the use of full breast radiation. This imparts radiotherapy to the entire area of the breast. Radiation of the breast necessarily involves surrounding structures such as, but not limited to, the heart, lungs, esophagus, chest wall, ribs and other structures that are in close proximity to the breast. Thus, a new concept of only partial breast radiation has grown in popularity and involves the use of balloon catheters to treat cancer in the lumpectomy cavity, which studies thus far indicate is as effective as full breast radiation and eliminates damage to the surrounding organs.

Partial breast radiation is currently being delivered through balloon catheters placed into the lumpectomy cavity at the time of surgery or later under ultrasound guidance. This process of using a balloon catheter for radiation treatment involves placing a radioactive seed or source down the indwelling catheter for a brief period of time. Unfortunately, this method of utilizing a catheter and radioactive seed has a number of disadvantages. For instance, utilizing a concentrated dose of radiation over a short period of time in the form of a radioactive seed planted through means of the catheter creates a multitude of side effects, such as fat necrosis, seromas, hematomas, infection, and undesirable cosmetic outcomes. The use of partial breast radiation balloon catheters also requires additional expensive equipment to maintain and direct the source of the radiation into the partial breast balloon catheter, which is not available at all radiation sites.

Currently, the other source of breast radiation is full breast radiation by external beam equipment. The external beam radiation equipment is excellent for solid organs, such as a liver that contains a small tumor or the head of a pancreas that contains a small tumor. These tumors are most effectively treated with external beam radiation by placing a target or a metallic marker into the area of the tumor, which allows the external beam to be focused on this tumor and avoid damage to the surrounding tissue. These solid organs are rigid and do not move during the radiation treatment. However, the breast is an external structure, consisting primarily of fatty tissue, unlike the liver and pancreas.

Of note, the use of metallic markers in the breast tissue creates an unstable environment for the marker, and the marker does not necessarily remain in place or in a constant location. Consequently, in fatty tissue, these small seeds or targets may move from the intended target site, rendering the therapy ineffective. Thus, in order to utilize external beam radiation on the breast, a stable target must be available.

BRIEF SUMMARY OF THE INVENTION

Embodiments of the present invention address deficiencies of the art in respect to radiation treatments for cancer and provide a new and novel system for delivering radiation to a target. In an embodiment of the invention, a radiation target can be provided, which includes an implant. The implant can include a marker comprising a channel defined therethrough from one end of the marker to an opposite end of the marker, a single non-looping suture thread disposed within the channel, and a coating applied to both the single non-looping suture thread and also the marker.

Additional aspects of the invention will be set forth in part in the description which follows and in part will be obvious from the description, or it may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention, and together with the description they serve to explain the principles of the invention. The embodiments illustrated herein are presently preferred with it being understood, however, that the invention is not limited to the precise arrangements and instrumentalities shown, wherein:

FIG. 4A is an isometric view of another embodiment of an implant for use in a radiation targeting system of the present invention;

FIG. 5 is a perspective view of one embodiment of an introducer for use in a radiation targeting system of the present invention;

FIG. 6A is an isometric view of one embodiment of an introducer for use in a radiation targeting system of the present invention;

FIG. 6B is a top view of the introducer of FIG. 6A;

FIG. 6C is a side view of the introducer of FIG. 6A;

FIG. 6D is a front view of the introducer of FIG. 6A;

FIG. 7A is an isometric view of a loader for use in a radiation targeting system of the present invention;

FIG. 7B is a top view of the loader of FIG. 7A;

FIG. 7C is a side view of the loader of FIG. 7A;

FIG. 7D is a front view of the loader of FIG. 7A;

DETAILED DESCRIPTION OF THE INVENTION

Embodiments of the invention provide for a radiation targeting system used during external beam radiation therapy (EBRT) that can be delivered though a multi-directional stereotactic radiation source. The radiation targeting system can include a radiation target, which includes an implant. The implant can include a marker comprising a channel from one end of the marker to an opposite end of the marker, a single non-looping suture thread disposed within the channel, and a coating applied to both the single non-looping suture thread and also the marker. In this way, the implant can be a target for EBRT for organs that are composed of primarily fatty tissue, such as the breast, or other organs, like the prostate, liver, and pancreas, where a stable environment for placement of a non-moving target is needed.

Figure 1:
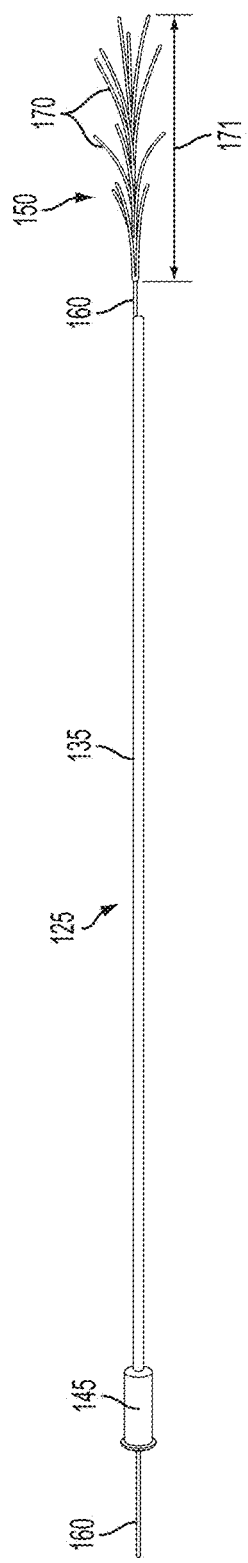
FIG. 1 is a perspective view of one embodiment of a radiation targeting system.

In illustration, FIG. 1 is a perspective view of one embodiment of a radiation targeting system. The system can comprise an introducer 125 and an implant 150. The introducer 125 can include a cannula 135. On one end of the cannula 135 can be a port 145. The implant 150 can be disposed within the cannula 135 of the introducer 125 and can include a wire stem 160 and multiple different wire branches 170, each extending outwardly from a proximal portion 171 of the wire stem 160 towards the proximal portion 171 of the wire stem 160. The implant 150 can be radio-opaque and may or may not be biodegradable. Both the introducer 125 and the implant 150 can be manufactured by any technique now known or later developed. In addition, both the introducer 125 and the implant 150 can be made of any metallic material, suitably sterilized, or other biocompatible material, including but not limited to stainless steel, gold, ceramic, platinum iridium, titanium, and nickel titanium.

Figure 2:
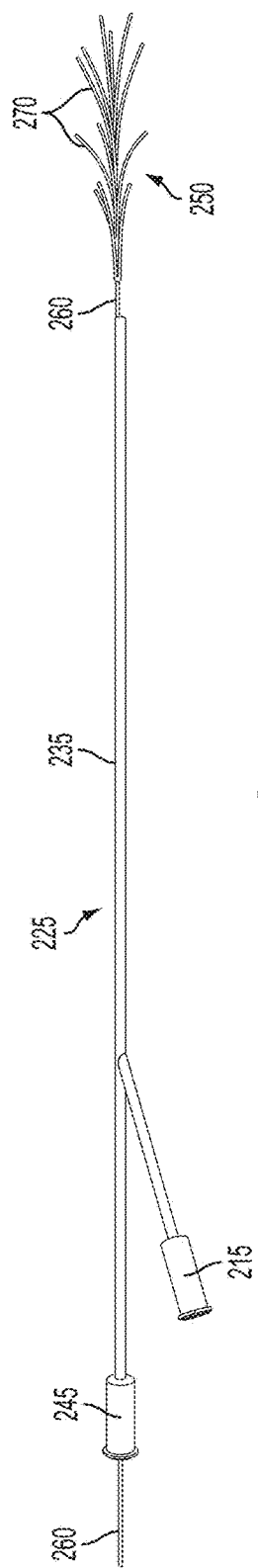
FIG. 2 is a perspective view of another embodiment of a radiation targeting system.

If further illustration, FIG. 2 is a perspective view of another embodiment of a radiation targeting system, which can include an introducer 225 comprising a cannula 235. The cannula 235 can include a port 245 at one end and an aperture in which an implant 250 can be inserted into the port 245 of the introducer 225. The introducer 225 can also include a side port 215. The side port 215 can be used to introduce fluids, such as saline, or to aspirate fluids or air from a lumpectomy cavity. Of note, in this way, by aspirating any fluid or air from the cavity, the tissue surrounding the cavity can collapse around the implant 250 and conform to the size and shape of the implant 250. The implant 250 can comprise a wire stem 260 and multiple different wire branches 270.

Figure 3A:
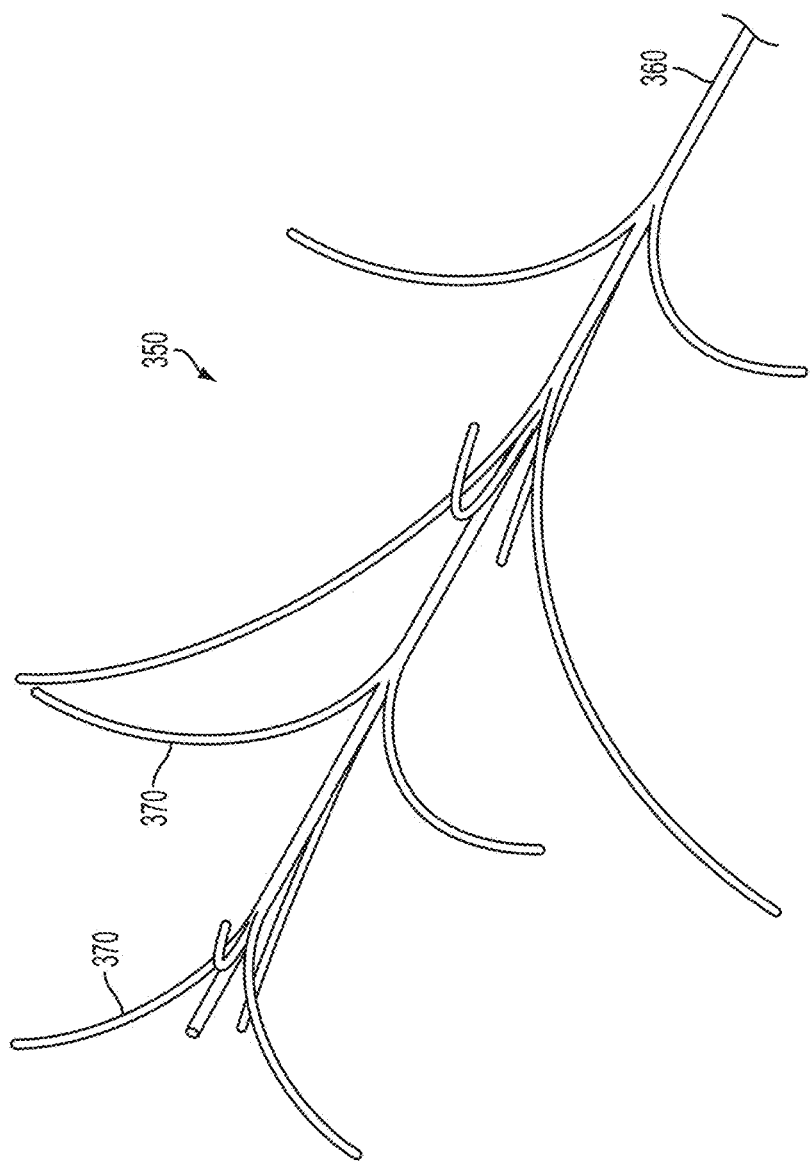
FIG. 3A is an isometric view of one embodiment of an implant for use in a radiation targeting system of the present invention.

In yet further illustration, FIG. 3A is an isometric view of one embodiment of an implant 350 for use in a radiation targeting system of the present invention. The implant 350 can be radio-opaque and can comprise a wire stem 360 and multiple different wire branches 370, each extending outwardly from a proximal portion of the wire stem 360 towards the proximal portion of the wire stem 360. Of note, the wire branches 370 can be arched. Of further note, an implant 350 can be manufactured in a variety of sizes and shapes. In addition, an implant 350 is not limited to a specific number of wire branches 370: for instance, there can be one wire branch 370 that is helical-shaped, multiple wire branches 370 that are spherical-shaped, multiple wire branches 370 that are helical-shaped, etc. Optionally, the implant 350 can include growth stimulators and/or stem cells. In addition, the implant 350 can be treated in any way now known or later developed so that tissue does not stick to it; in one instance, the implant 350 can be highly polished. Of note, the implant 350 can be placed, with or without an introducer, in the body during surgery (following a lumpectomy or other procedure) or after any procedure using ultrasound guidance.

Figure 3B:
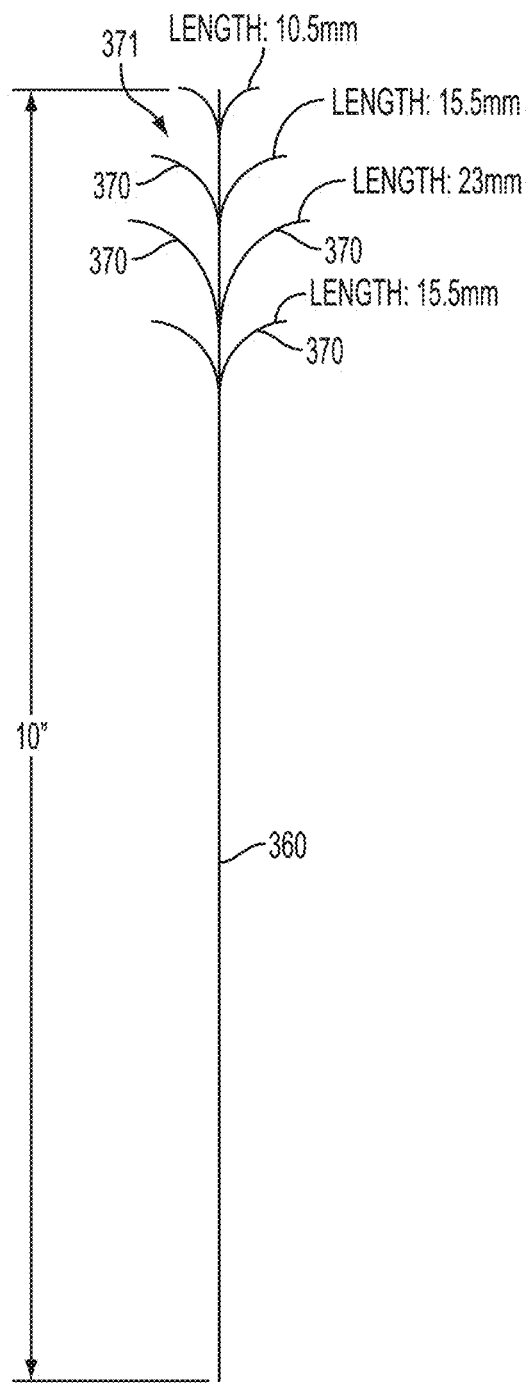
FIG. 3B is a top view of the implant of FIG. 3A.

In even further illustration, FIG. 3B is a top view of the implant 350 of FIG. 3A. At a proximal portion 371 of a wire stem 360, multiple wire branches 370 can extend outwardly. As illustrated in FIG. 3B, the implant can be ten inches in length with a first set of branches comprising a length of at least ten and one-half millimeters, a second and fourth set of branches comprising a length of at least fifteen and one-half millimeters, and a third set of branches comprising a length of twenty-three millimeters.

Figure 3C:
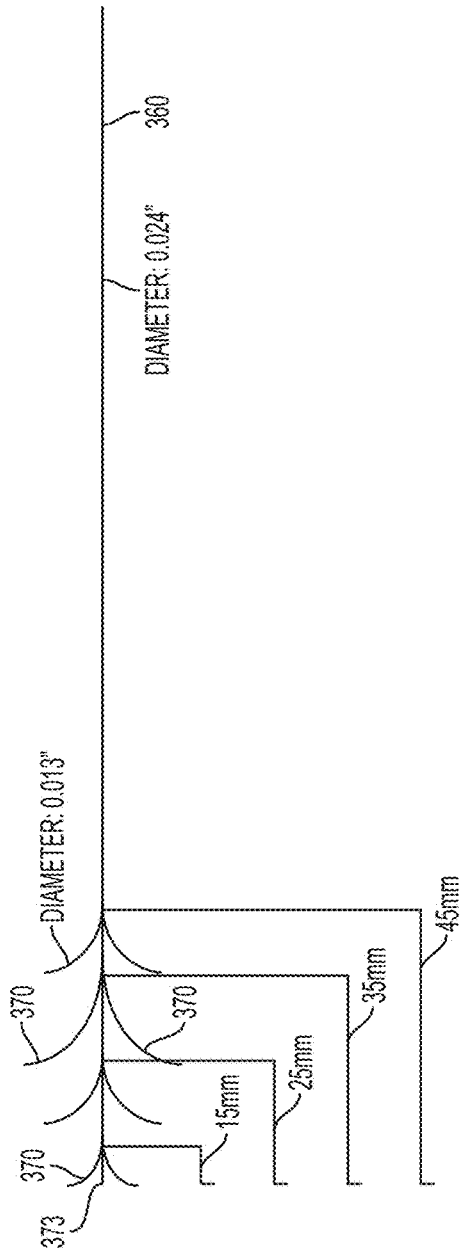
FIG. 3C is a side view of the implant of FIG. 3A.

In even yet further illustration, FIG. 3C is a side view of the implant 350 of FIG. 3A. The wire stem 360 can have a diameter of at least 0.024 inches and the multiple different wire branches 370 can have a diameter of at least 0.013 inches. The wire branches 370 can be coupled to the wire stem 360 at a variety of distances; in one instance, the distance from a tip 373 of the wire stem 360 to a first set of branches can be at least fifteen millimeters, from the tip 373 to a second set of branches can be at least twenty-five millimeters, from the tip 373 to a third set of branches can be at least thirty-five millimeters, and from the tip 373 to a fourth set of branches can be at least forty-five millimeters. Of note, the wire branches 370 can be attached to the wire stem 360 by any method now known or later developed, including but not limited to welding and crimping. Of further note, individual wire branches 370 can be directly coupled to the wire stem 360 or individual wire branches 370 can be grouped together to form sets of wire branches 370, which can then be attached to the wire stem 360 using any method now known or later developed. In one instance, four individual wire branches 370 can form a set of wire branches 370 and there can be four sets of wire branches 370 coupled to the wire stem 360.

Figure 3D:
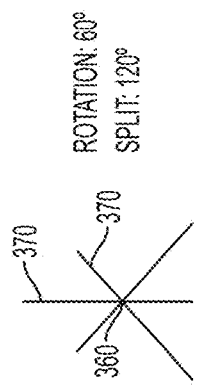
FIG. 3D is a front view of the implant of FIG. 3A.

FIG. 3D is a front view of the implant 350 of FIG. 3A. Wire branches 370 can be positioned around a wire stem 360 so that there is about a sixty degree rotation between each wire branch 360. In addition, there can be a split of about one hundred twenty degrees.

In further illustration, FIG. 4A is an isometric view of another embodiment of an implant 450 for use in a radiation targeting system of the present invention. The implant 450 can be radio-opaque and can comprise a wire stem 460 and multiple different wire branches 470, each extending outwardly from a proximal portion of the wire stem 460 towards the proximal portion of the wire stem 460. Coupled to one end of at least one wire branch 470 can be a marker 490. Of note, the marker 490 is not limited to attachment at an end of each wire branch 470. In addition, a marker 490 does not need to be coupled to every wire branch; a marker 490 can be coupled to one, all, or as many as the wire branches 480 as needed. The marker 490 is not limited to a specific size or shape; for instance the marker 490 can be a non-radioactive seed, which can be made from any radio-opaque material, including but not limited to gold, platinum iridium, and titanium. The marker 490 can also be round, like a ball. Of note, multiple different marker materials can be contained within an implant 450; for instance, an implant 450 may be comprised of a nickel titanium wire stem 460 and wire branches 470 with gold seeds coupled to the ends of the wire branches 470. Of further note, the wire branches 470 can be arched. Of even further note, an implant 450 can be manufactured in a variety of size and shapes. In addition, an implant 450 is not limited to a specific number of wire branches 470, for instance, there can be one wire branch 470 that is helical-shaped, multiple wire branches 470 that are spherical-shaped, multiple wire branches 470 that are helical-shaped, etc. Optionally, the implant 450 can include growth stimulators and/or stem cells. In addition, the implant 450 can be treated in any way now known or later developed so that tissue does not stick to it; in one instance, the implant 450 can be highly polished.

Figure 4B:
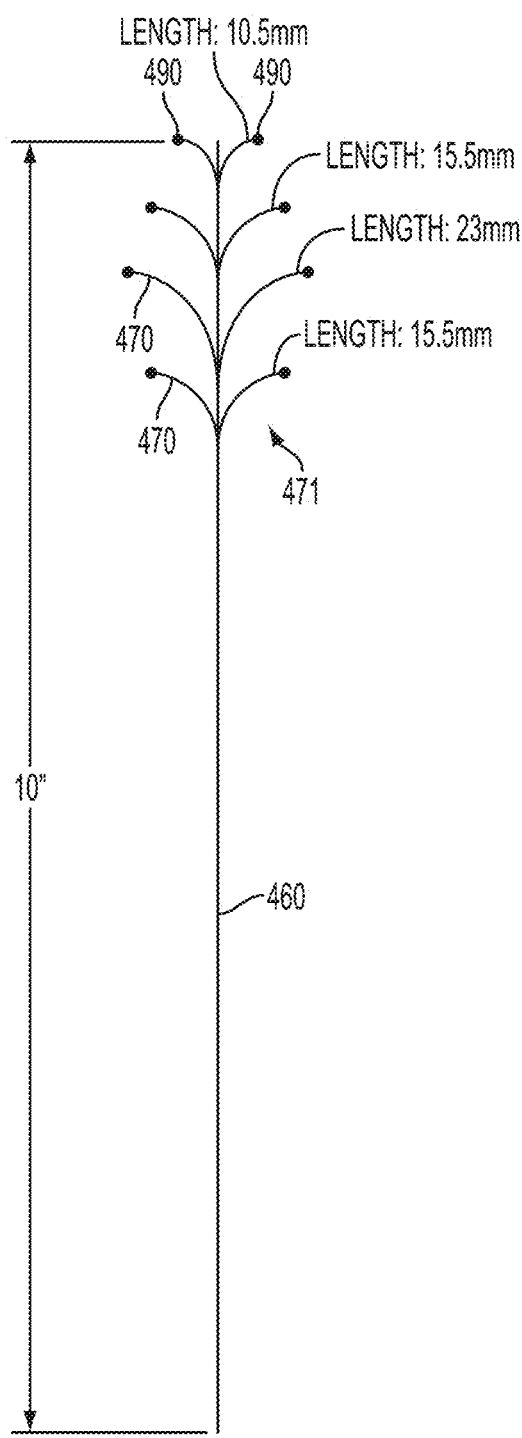
FIG. 4B is a top view of the implant of FIG. 4A.

In yet even further illustration FIG. 4B is a top view of the implant 450 of FIG. 4A. At a proximal portion 471 of a wire stem 460, multiple wire branches 470 can extend outwardly. The wire stem 460 can be at least ten inches in length and can have a diameter of at least 0.024 inches. As illustrated in FIG. 4B, the implant can have a first set of branches comprising a length of at least ten and one-half millimeters, a second and fourth set of branches comprising a length of at least fifteen and one-half millimeters, and a third set of branches comprising a length of twenty-three millimeters. In addition, a marker 490 can be coupled to one end of at least one wire branch 470; in other words, a marker 490 does not need to be coupled to each wire branch 470.

Figure 4C:
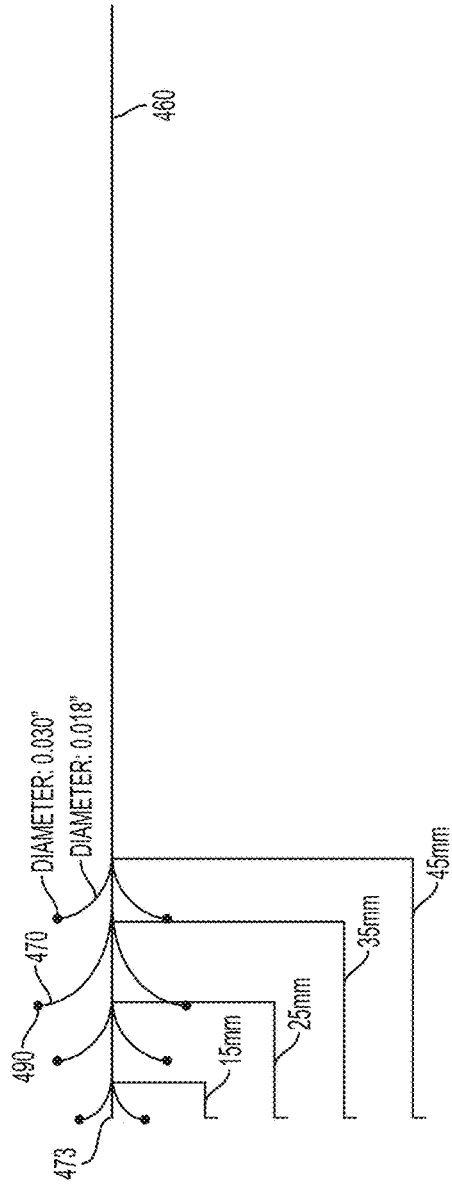
FIG. 4C is a side view of the implant of FIG. 4A.

FIG. 4C is a side view of the implant 450 of FIG. 4A. The multiple different wire branches 470 can have a diameter of at least 0.018 inches. A marker 490 can be coupled to the wire branch 470, can be of any shape and size, and in one embodiment, can be a ball with a diameter of at least 0.030 inches. In another embodiment, the marker 490 can be a non-radioactive seed. The wire branches 470 can be coupled to the wire stem 460 at a variety of distances; in one instance, the distance from a tip 473 of the wire stem 460 to a first set of branches can be at least fifteen millimeters, from the tip 473 to a second set of branches can be at least twenty-five millimeters, from the tip 473 to a third set of branches can be at least thirty-five millimeters, and from the tip 473 to a fourth set of branches can be at least forty-five millimeters. Of note, the wire branches 470 can be attached to the wire stem 460 by any method now known or later developed, including but not limited to welding and crimping. Of further note, individual wire branches 470 can be directly coupled to the wire stem 460 or individual wire branches 470 can be grouped together to form sets of wire branches 470, which can then be attached to the wire stem 460 using any method now known or later developed. In one instance, four individual wire branches 470 can form a set of wire branches 470.

Figure 4D:
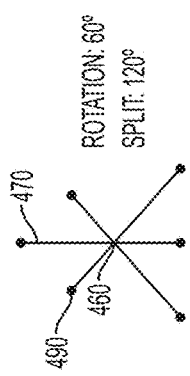
FIG. 4D is a front view of the implant of FIG. 4A.

In yet even further illustration, FIG. 4D is a front view of the implant 450 of FIG. 4A. Wire branches 470 can be positioned around a wire stem 460 so that there is about a sixty degree rotation between each wire branch 460. Attached to at least one of the wire branches 460 can be a marker 480. In addition, there can be a split of about one hundred twenty degrees.

In further illustration FIG. 5 is a perspective view of one embodiment of an introducer 525 for use in a radiation targeting system of the present invention. The introducer 525 can be comprised of a cannula 535. On one end of the cannula 535 can be a port 545 and on the opposite end of the cannula 535 can be an aperture 536. Of note, in use, the port 545 is generally at the end of the cannula 535 opposite to the aperture 536 that enters a body to enable an implant to be placed within the body. An implant can be disposed within the cannula 535 of the introducer 525. An implant can also be adapted for insertion into a port 545 of the introducer 525. A side port 515 can also be coupled to the cannula 535. Of note, in one instance, the cannula 535 can be bifurcated, where one port 545 is coupled to one part of the bifurcation fork and a side port 515 is coupled to a second part of the bifurcation fork. In another instance, a tube can be coupled to the cannula 535 and the side port 515 can be coupled to the end of the tube not attached to the cannula 535. In either case, a channel is maintained between the fork where the side port 515 is coupled to the cannula 535 in order to allow materials to pass, including but not limited to air, fluid, and medical instruments. Of further note, the introducer 525 can be made of any metallic material, suitably sterilized, or other biocompatible material, including but not limited to stainless steel, gold, platinum iridium, ceramic, titanium, and nickel titanium In further illustration, FIG. 6A is an isometric view of one embodiment of an introducer 625 for use in a radiation targeting system of the present invention. The introducer 625 can include a cannula 635. The cannula 635 can include a port 645 at one end of the cannula 635 and an aperture 636 at an opposite end of the cannula 635. The port 645 can include a locking apparatus; for instance, a lever lock, which can secure an instrument to the introducer 625 or a trocar can be instructed through the port 645 and secured in place to the introducer 625. More specifically, the trocar can contain a male component on one end that can be screwed into a female component on the port 645, thus securing the trocar in the introducer 625. Optionally, a side port 615 can be coupled to a tube 617, which can be coupled to the cannula 635 of the introducer 625. The tube 617 can be coupled to the cannula 635 using any method now known or later developed, including but not limited to welding. In addition, the cannula 635 with the coupled tube 617 can be manufactured as one piece. The side port 615 can include a seal. In this way, an instrument can be coupled to the seal so as to aspirate air or fluids from a cavity. In addition, an instrument can be coupled to the side port 615, with or without a seal, which can introduce fluids into the cavity or into a component; for instance, a balloon attached to an implant or the introducer 625. The side port 615 can also include a locking apparatus. The introducer 625 can be made from any metallic material, suitably sterilized, or other biocompatible material, including but not limited to stainless steel, gold, ceramic, titanium, platinum iridium, and nickel titanium In yet further illustration, FIG. 6B is a top view of the introducer 625 of FIG. 6A. The introducer can include a cannula 635 coupled to a tube 617. The tube 617 can have a length of at least 1.375 inches and can have an inner diameter of at least 0.060 inches and an outer diameter of at least 0.079 inches. A side port 615 can be coupled to on one end of the tube 617. In addition, the distance from the attachment point between the tube 617 and the cannula 635 to the end of a port 645 coupled to one end of the cannula can be at least two and one-half inches. Also, the angle between the cannual 635 and the tube 617 can be at least thirty degrees. The cannula 635 can include an aperture 636 at an opposite end of the port 645. Of note, the end of the cannula 635 defining the aperture 636 can be pointed or can be flat; in other words, the end of the cannula 635 can be sharp in order to make an opening in skin so that an implant can be introduced to the body or the end of the cannula 635 can be dull requiring another instrument, such as a trocar, to be used, whether or not in conjunction with the introducer.

FIG. 6C is a side view of the introducer 625 of FIG. 6A. The introducer 635 can include a cannula 635 having a length of at least eight and one-half inches and an inside diameter of 0.060 inches and an outer diameter of 0.070 inches. Attached to the cannula 635 on one end can be a port 645. A side port 615 can also be coupled to the cannula 635.

In yet even further illustration, FIG. 6D is a front view of the introducer 635 of FIG. 6A showing a port 645 and a side port 615 coupled to a tube 617.

In further illustration, FIG. 7A is an isometric view of a loader 730 for use in a radiation targeting system of the present invention. The loader 730 can include a tube 731 with an aperture 733 at one end of the tube 731 and a tip 732 at an opposite end of the tube 731. The loader 730 can be made of any material now known or later developed, including but not limited to stainless steel, ceramic, and titanium. Of note, the tip 732 can include an outer diameter that tapers from a distal end of the tip 732 with a diameter smaller than a diameter of the cannula of the introducer, towards the opposite end of the tip 732 with a diameter that is equal to or greater than the diameter of the cannula of the introducer. In use, the loader 730 can be used to load the implant into the introducer. Of note, if the optional loader 730 is used, a portion of the implant remains on the outside of the loader 730; in other words, only a portion of the implant is inserted into the loader 730.

In further illustration, FIG. 7B is a top view of the loader 730 of FIG. 7A. A tube 731 can have an inner diameter of at least one and one-half millimeters and an outer diameter of at least two millimeters. The tube 731 can include an aperture 733 on one end and at an opposite end a tip 732. The tip 732 can include an inner diameter of at least 0.150 inches. The tip 732 can also include an outer diameter of at least 0.150 at a distal end of the tip 732 that tapers to a diameter smaller than a diameter of the cannula of the introducer towards the opposite end of the tip 732 with a diameter that is equal to or greater than the diameter of the cannula of the introducer. In this way, the loader 730 is adapted to fit into the port of the introducer and because of the size difference between the tapering of the outer diameter of the loader and the inner diameter of the port of the introducer, the loader is prevented from moving further into the port of the introducer; this allows the implant to be inserted through the port of the introducer into the cannula of the introducer.

FIG. 7C is a side view of the loader 730 of FIG. 7A illustrating that the loader can be at least four inches in length with the tip 732 having a length of 0.3 inches, thus making the length of the tube 731 about 3.7 inches.

In yet even further illustration, FIG. 7D is a front view of the loader 730 of FIG. 7A.

Figure 8:
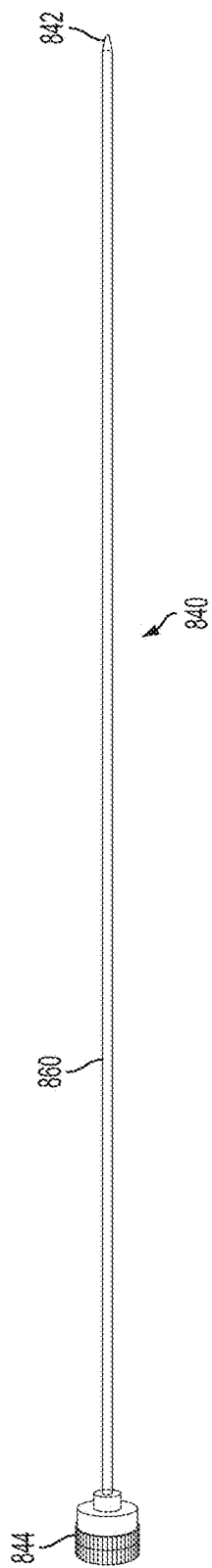
FIG. 8 is a perspective view of a trocar for use in a radiation targeting system of the present invention.

In further illustration, FIG. 8 is a perspective view of a trocar 840 for use in a radiation targeting system of the present invention. The trocar 840 can include a wire stem 860 with a tip 842 at one end and a top 844 at an opposite end of the wire stem 860. Of note, the top 844 can be locked so as to be securely attached to a port of an introducer. In other words, the trocar 840 can include a male locking component that locks into a female receiver on the introducer. Of note, the female receiver can be part of the port on the introducer. The trocar 840 can be of any length so that it can be inserted into the introducer of the radiation targeting system; the trocar 840 is adapted for insertion through the cannula of the introducer. The trocar 840 can be made of any material now known or later developed, including but not limited to stainless steel, ceramic, and titanium. Of note, the trocar 840 would normally not be used if an implant is placed using an introducer in a body during surgery; although, a trocar 840 would likely be used when placing the implant using ultrasound guidance post-operation.

Figure 9A:
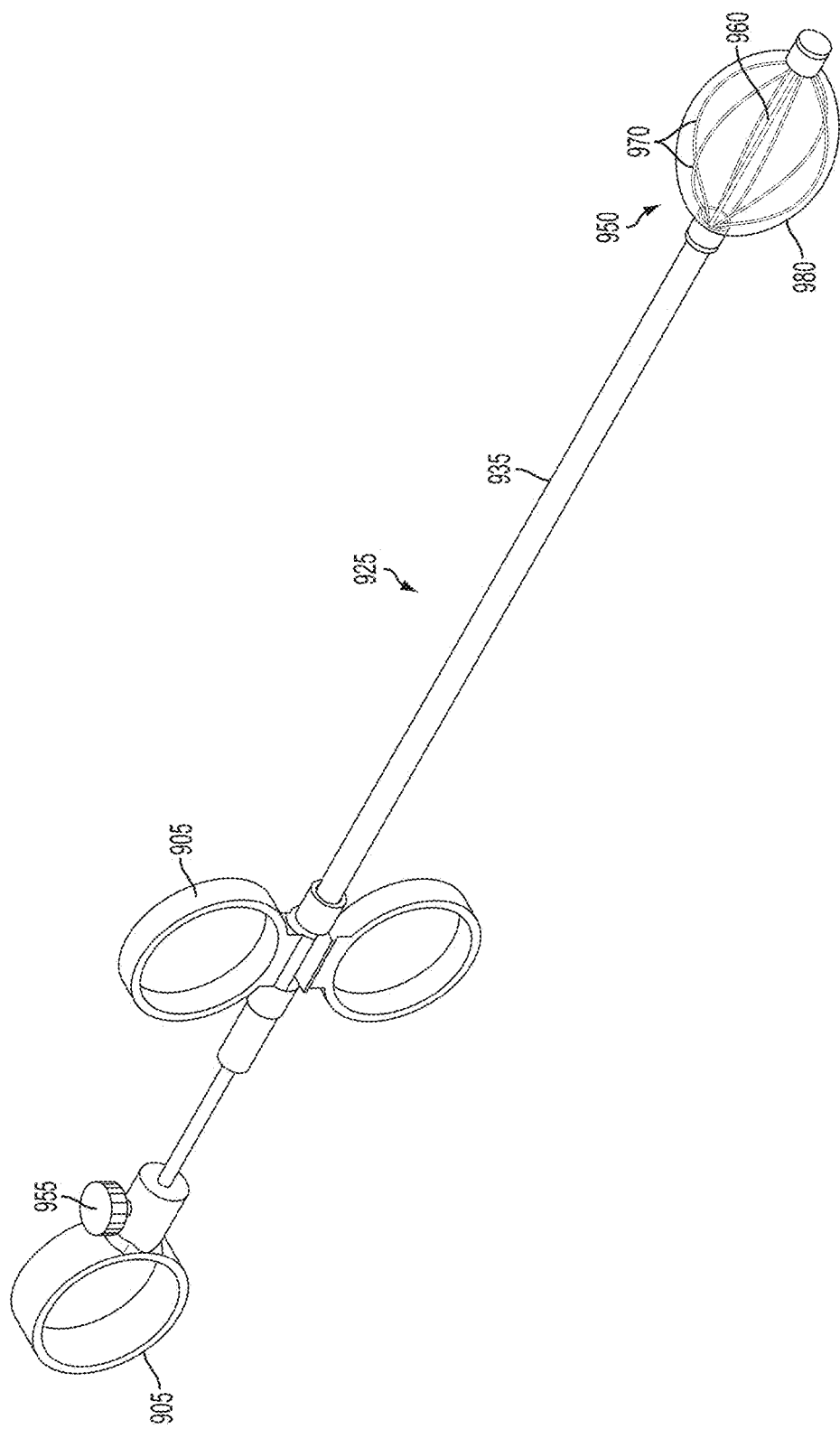
FIG. 9A is a perspective view of one embodiment of a radiation targeting system.
Figure 9B:
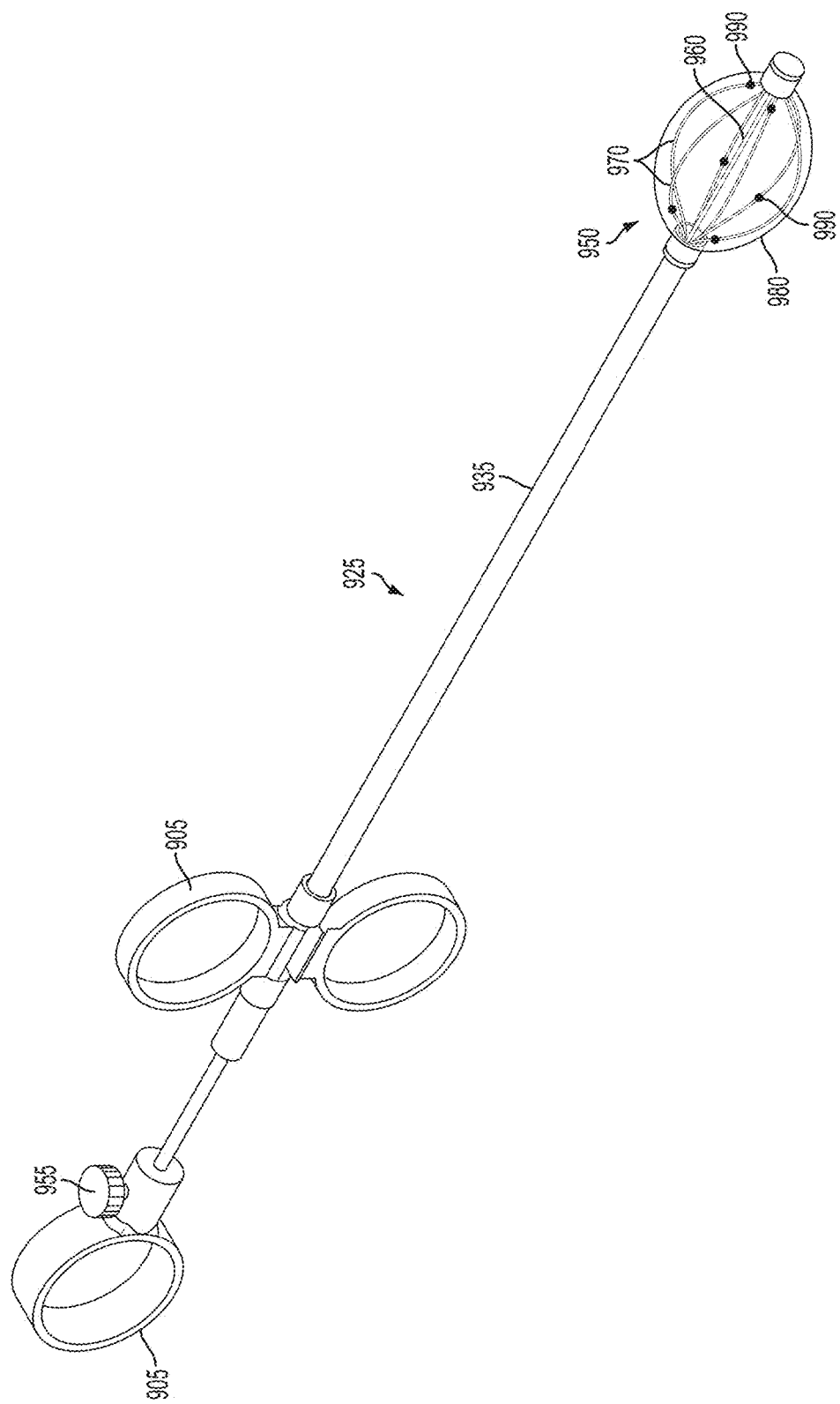
FIG. 9B is a perspective view of another embodiment of a radiation targeting system.

In even further illustration, FIGS. 9A and 9B are each perspective views of embodiments of a radiation targeting system that can include an introducer 925 that can further include a cannula 935. The introducer 925 can include a plurality of finger rings 905 and a valve 955. The valve 955 can be used to inflate a balloon 980. The balloon 980 can be coupled to a plurality of wire branches 970 and a wire stem 960. In other words, there can be at least two wire branches 970. Optionally, the wire branches 970 can be coupled to at least one marker 990, as shown in FIG. 9B. The marker 990 can be coupled to every wire branch 970, just one wire branch 970, or somewhere in between. In addition, the marker 990 can be coupled anywhere on the wire branch 970; for instance, the marker 990 can be coupled toward an end of the wire branch 970, in the middle of the wire branch 970, or somewhere in between. Also, there can be multiple markers 990 on each wire branch 970, no marker 990 on a wire branch 970, or any combination thereof. For instance, if there are a total of eight wire branches 970, there may be one marker 990 on four wire branches 970, no marker on two wire branches 970, and two markers 990 on the remaining two wire branches 970. A marker 970 is not limited to a specific size or shape; for instance, the marker 970 can be a non-radioactive seed, which can be made from any radio-opaque material, including but not limited to ceramic, gold, platinum iridium, and titanium. The marker 990 can also be round, like a ball. The balloon 980, the wire branches 970, the wire stem 960, and the marker 990, if present, can be components of an implant 950 in an embodiment of a radiation targeting system. Further, the balloon 980, the wire branches 970, the wire stem 960, and the marker 990 can each be any size (length, diameter, width, etc.). Of further note, the balloon 980 can provide support to a lumpectomy cavity. In addition, the balloon 980 can be coated with a material to prevent tissue from sticking to the balloon 980.

Figure 10A:
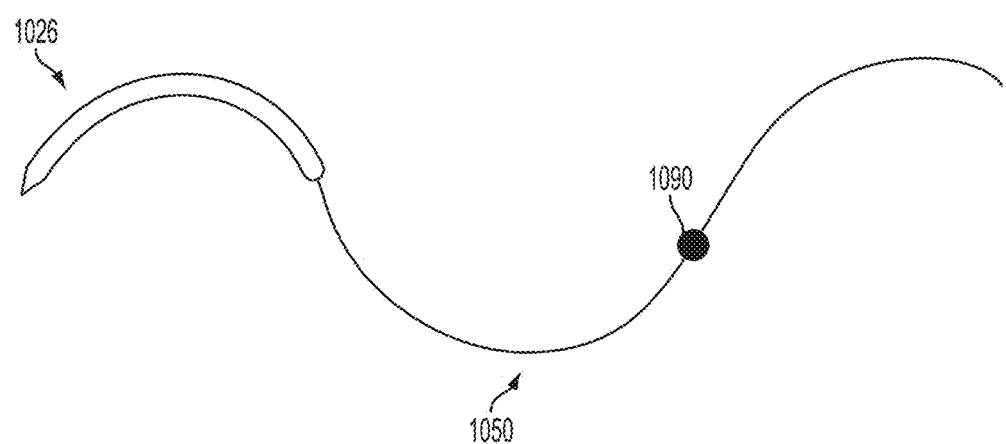
FIG. 10A is a line drawing of one embodiment of an implant for use in a radiation targeting system of the present invention.
Figure 10B:
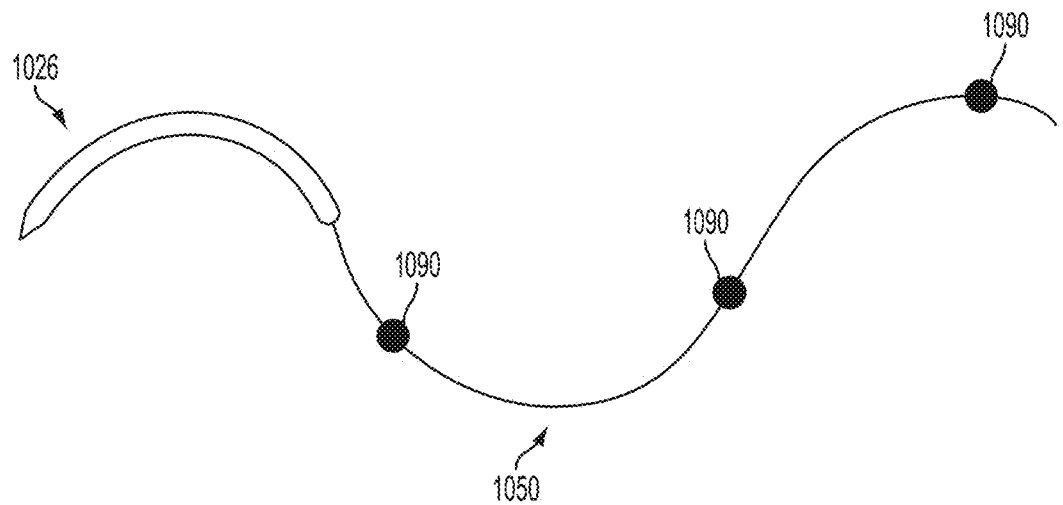
FIG. 10B is a line drawing of one embodiment of an implant for use in a radiation targeting system of the present invention.

In yet even further illustration, FIGS. 10A and 10B are line drawings of embodiments of implants 1050 for use in a radiation targeting system of the present invention that can include a needle 1026 coupled to an implant 1050 where as the implant 1050 can be further coupled to a marker 1090. The needle 1026 is not limited to a particular type, size, shape, or material. In one instance, the needle 1026 can be a cannula. In one embodiment, the implant 1050 can be suture thread made from any material now known or later developed, including but not limited to catgut, silk, nylon, and polypropylene. The implant 1050 can be absorbable or non-absorbable. The length and diameter of the implant 1050 are not specifically defined, so long as the implant 1050 can be securely fastened in place in a body cavity. In this way, the implant 1050 serves to stabilize a marker 1090, which enables the marker 1090 to serve as a stable target for EBRT in a breast, body cavity, or other organ. The marker 1090 is not limited to a specific diameter or shape; for instance, in one embodiment the marker 1090 can be a non-radioactive seed. In another embodiment, the marker 1090 can be round, like a ball. The marker 1090 can be made from any radio-opaque material, including but not limited to ceramic, gold, platinum iridium, and titanium. Of note, each implant 1050 can have at least one marker 1090; in other words, multiple markers 1090 can be coupled to each implant 1050, as shown in FIG. 10B. Of further note, multiple implants 1050, each coupled to at least one marker 1090, can be attached in a body cavity. Regardless of the number of implants 1050, an implant 1050 can be used to stabilize any markers 1090 coupled to the implant 1050 so that the markers 1090 can serve as a target for the radiation beam during EBRT. The marker 1090 can be coupled to the implant 1050 in any method now known or later developed. In addition, the marker(s) 1090 can be coupled to the implant 1050 at any position along the implant 1050. Of further note, in another embodiment, the implant 1050 can be radio-opaque with no marker 1090 attached to it; in other words, the implant 1050 (the suture thread itself) can serve as the target. Of even further note, the needle 1026 along with the implant 1050 can be pushed into tissue by hand or may be loaded, including back loaded, into an applicator, loader, introducer, or other component; in other words, the implant 1050 may be inserted directly into tissue or a body cavity without using another component, such as an applicator, loader, or introducer.

Figure 10C:
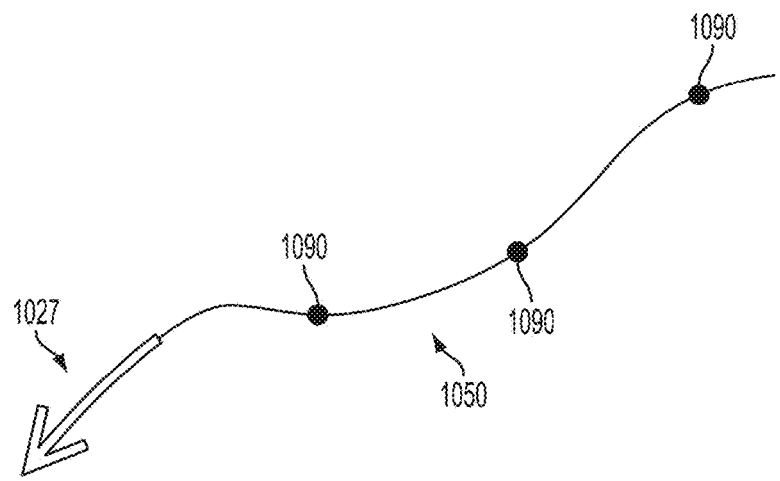
FIG. 10C is a line drawing of one embodiment of an implant for use in a radiation targeting system of the present invention.

In even further illustration, FIG. 10C is a line drawing of one embodiment of an implant 1050 for use in a radiation targeting system of the present invention that can include a barb 1027 coupled to an implant 1050; the implant 1050 can be further coupled to a marker 1090. The barb 1027 is not limited to a particular type, size, shape, or material. Of note, the barb 1027 along with the implant 1050 can be pushed into the tissue by hand or may be loaded, including back loaded, into an applicator, loader, introducer, or other component. In one embodiment, the implant 1050 can be suture thread made from any material now known or later developed, including but not limited to catgut, silk, nylon, and polypropylene. The implant 1050 can be absorbable or non-absorbable. The length and diameter of the implant 1050 are not specifically defined, so long as the implant 1050 can be securely fastened in place in a body cavity. In this way, the implant 1050 serves to stabilize a marker 1090, which enables the marker 1090 to serve as a stable target for EBRT in a breast, body cavity, or other organ. The marker 1090 is not limited to a specific diameter or shape; for instance, in one embodiment the marker 1090 can be a non-radioactive seed. In another embodiment, the marker 1090 can be round, like a ball. The marker 1090 can be made from any radio-opaque material, including but not limited to platinum iridium, ceramic, gold, and titanium. Of note, an implant 1050 can have no markers 1090 or, as shown in FIG. 10C, at least one marker 1090; in other words, multiple markers 1090 can be coupled to each implant 1050, as shown in FIG. 10C. Of further note, multiple implants 1050, each coupled to at least one marker 1090, can be attached in a body cavity. Regardless of the number of implants 1050, an implant 1050 can be used to stabilize any markers 1090 coupled to the implant 1050 so that the markers 1090 can serve as a target for the radiation beam during EBRT. The marker 1090 can be coupled to the implant 1050 in any method now known or later developed. In addition, the marker(s) 1090 can be coupled to the implant 1050 at any position along the implant 1050. Of further note, in another embodiment, the implant 1050 can be radio-opaque with no marker 1090 attached to it; in other words, the implant 1050 (the suture thread itself) can serve as the target.

Figure 11:
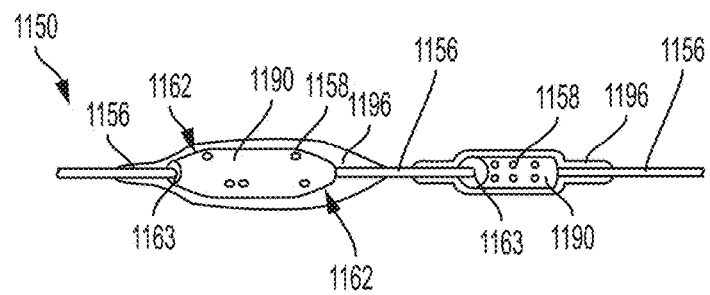
FIG. 11 illustrates a different embodiment of an implant for use in a radiation targeting system.

In yet further illustration of the invention, FIG. 11 illustrates a different embodiment of an implant 1150 for use as a radiation target in a radiation targeting system. As pictured in FIG. 11, the implant 1150 can include one or more markers 1190 coupled to a suture thread 1156. In one embodiment, the implant 1150 can include a single non-looping suture thread 1156 that can be passed once through a channel 1163 defined along a central longitudinal axis through one end of a marker 1190 to an opposite end of the marker 1190, such that the single non-looping suture thread 1156 extends past both ends of the marker 1190. In a different embodiment, the implant 1150 can include a single non-looping suture thread 1156 first disposed within the channel 1163 of one marker 1190 and then the non-looping suture thread 1156 can proceed through the channel 1163 of a different marker 1190 and so on, such that the implant 1150 includes more than one marker 1190, but only one non-looping suture thread 1156, as illustrated in FIG. 11. In a different embodiment, the non-looping suture thread 1156 can include multiple suture threads (pieces of) coupled to each other to form a larger single suture thread 1190. In another embodiment, the non-looping suture thread 1156 can include multiple suture threads, where one end of a non-looping suture thread 1156 is coupled to an end of one marker 1190 and to an end of a different marker 1190, such that there are no suture threads 1156 disposed within the marker 1190. Of note, non-looping refers to the suture thread 1156 not being looped or tied prior to the implantation of the implant 1150 into a body cavity, tissue, or organ. However, after implantation, the implant 1150 may be secured in the body by looping (tying) the suture thread 1156 to a portion of the body (whether in a cavity, to tissue, or to an organ). Of note, in embodiments where an implant 1150 has two or more markers 1190, the space (distance) between each different marker 1190 is not specifically defined.

Additionally, the non-looping suture thread 1156 can be rigid or the suture thread 1190 can be elastic (flexible). In one embodiment, a non-looping suture thread 1156 can be considered rigid when the suture thread 1156 cannot be bent by a person using only hand strength, but the suture thread 1156 can be considered flexible when the suture thread 1156 can be bent by a person using hand strength. In a different embodiment, a suture thread 1156 can be considered rigid when it is made from polyethylene, included braided poly-blend polyethylene, and a suture thread 1156 can be considered flexible (elastic) when the suture thread 1156 is made from silk, nylon, or polyurethane. In yet a further embodiment, a suture thread 1156 can be considered flexible when the suture thread 1156 can be knotted (e.g. tied) by a person using hand strength only. Further, in a preferred embodiment, the suture thread 1156 can be absorbable.

Of note, the marker 1190 can be coupled to the non-looping suture 1156 by any method now known or later developed, including but not limited to cement, crimping, and wrapping. With respect to crimping, each end of a marker 1190 can be crimped (squeezed) resulting in tapered ends 1162 of the marker 1190 by using a specialized tool for crimping to secure any markers 1190 to the non-looping suture 1156. As such, each end of a marker 1190 that is coupled to the non-looping suture 1156 by crimping has an essentially elliptical cross section and an essentially circular cross section along an axis bisecting the marker into two equal halves. Of note, in a different embodiment, the entire marker 1190 has an essentially circular cross section along the longitudinal axis of the marker 1190, such that both the portions of the marker 1190 that are crimped and the section of the marker 1190 not crimped (between the end crimped portions of the marker 1190) have an essentially circular cross section. However, if the marker 1190 is not crimped to the non-looping suture 1156, the marker 1190 has an essentially circular cross section along the longitudinal axis of the marker 1190. With respect to wrapping, the marker 1190 can begin as a flat piece of material (see FIG. 14A), such as in the shape of a square or a rectangular, which is then wrapped around a suture thread 1156 to form a cylindrically shaped marker 1190. Of note, in some embodiments, when the marker 1190 is formed from wrapping, the material may or may not overlap as well as may or may not be bonded. More specifically, in an embodiment where a marker 1190 is made from metal, as the metal holds its shape when wrapped, the two edges of the metal may not be coupled (bonded), as the metal holds its shape. Besides radiopague metal, including gold, platinum iridium, titanium, stainless steel, titanium, and nickel titanium, the marker 1190 can be made from ceramic as well as a composite of different materials, including a composite of different radiopague (or radio-opague) metals. In addition, the marker 1190 can be both non-radioactive and also radio-opaque. Additionally, any marker 1190 can have any radius (or diameter), whether inner or outer as well as length. Also, for embodiments having more than one marker 1190, each marker 1190 on the non-looping suture 1156 can have different lengths and/or different radii (or diameters) or each marker 1190 can have the same length and also the same radii (or diameter). Further, the marker 1190 is non-absorbable by the body (human or animal).

In addition to the channel 1163 running the length of the marker 1190, the surface of the marker 1190 can define one or more apertures 1158. These apertures 1158 can be added to the marker 1190 by any method now known or later developed, including etching (see FIGS. 14A and 14B), stamping, and laser cutting (see FIG. 15). The apertures 1158 can be arranged on the surface of the marker 1190 in a pattern or randomly. Further, the number of specific apertures 1158 on the surface of a marker 1190 can vary. For example, in FIG. 11, the first marker (when read left to right) is shown as having five (5) randomly placed apertures 1158, and the second marker 1190 is shown as having six (6) apertures 1158 placed in a pattern. Though not shown, it should be understand that the side of the marker 1190 not pictured could also include zero or more apertures 1158 placed randomly or in a pattern.

In this way, when a radiation beam from an external beam radiation source is applied to (targeted at) the one or more markers 1190, the apertures 1158 on the marker 1190 disperse the radiation allowing for better imaging of the marker 1190 and, thus, a more accurate understanding of the margins of a body cavity, organ, tissue, or tumor. Of note, the number of apertures 1158 affects the scatter of aimed radiation. More specifically, in the case of a marker 1190 made from metal, the more metal, the more scatter. As such, the apertures 1158 add space, which affects the dispersement of radiation by reducing it. Therefore, the number of apertures 1158 can be varied to affect the scatter of radiation and, thus, be used to control such dispersement. Of note, an implant 1150 can include a combination of markers 1190, where some markers 1190 on the suture thread 1156 include apertures 1158 and some markers 1190 do not, as shown in FIG. 12.

In addition, a coating 1196 can be directly coupled to both the marker 1190 and also the suture 1156. More specifically, in one embodiment, the coating 1196 can be applied to only a portion of the suture 1156 and the entire outside surface of any markers 1190, as shown in FIG. 11. In other words, there can be a continuous coating 1196 that covers the marker 1190 and extends from at least a portion of the suture 1156 adjacent to one end of the marker 1190 to at least a portion of the suture 1156 past the opposite end of the marker 1190. In a different embodiment, the coating 1196 can be applied to the both the suture 1156 and the marker 1190, such that the entire outer surface of both the marker 1190 and the suture 1156 are covered with the coating 1196 (as illustrated in FIGS. 12 and 13). Additionally, the coating 1196 can be made from the same material as the suture 1156. The coating 1196 can further be a U.S. Food and Drug Administration (FDA) approved material. In this way, when the implant 1150 is inserted, it glides through the human body, such as tissue or organ. In other words, the coating 1196 reduces friction and assists in preventing portions of the human body from getting caught on the implant 1150.

Figure 12:
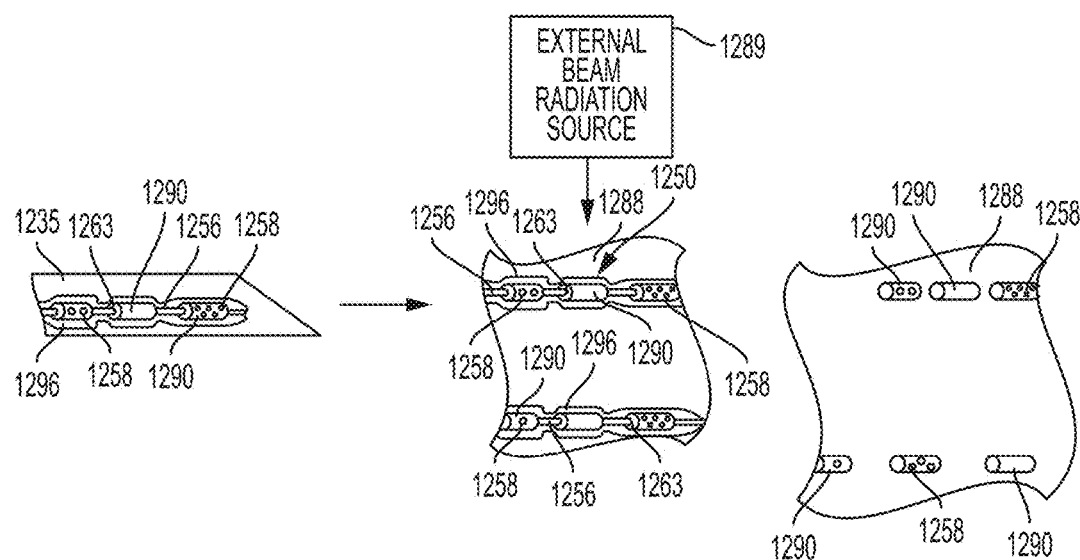
FIG. 12 illustrates the insertion of an embodiment of an implant into an organ of a body via a cannula.
Figure 13:
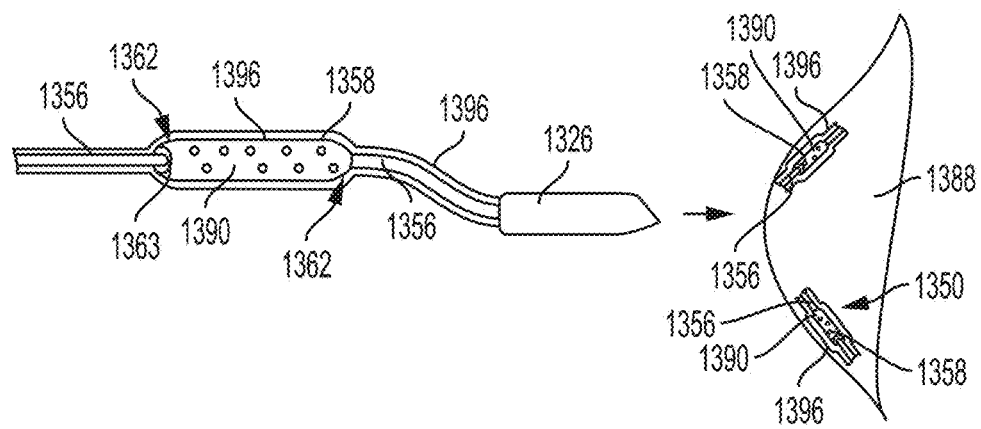
FIG. 13 illustrates another embodiment of an implant for use as a radiation target and the insertion of such into a body.

In yet further illustration of the invention, FIG. 12 demonstrates how an implant 1250 in a cannula 1235 can be transferred from the cannula 1235 to the human body, such as an organ 1288, including the prostate, liver, or pancreas as well as other solid organs. More specifically, one or more implants 1250 can include one or more markers 1290, with each marker 1290 having zero or more apertures 1258. Further, each marker 1290 is coupled to a suture thread 1256 disposed within a channel 1263 and extends past both ends of each marker 1290. Yet further, both the suture thread 1256, which in a preferred embodiment is non-looping, and the marker 1290 are covered by a coating 1296. As shown in FIG. 12, the coating 1296 can be continuous. More specifically, the continuous coating 1296 can cover each marker 1290 and extend, for each marker 1290, from at least a portion of the suture 1256 adjacent to one end of one marker 1290 to at least a portion of the suture 1256 past the opposite end of the same marker 1290. Of note, in this embodiment, a portion of the suture 1256 can include the entire suture 1256 not disposed within the channel 1263 of a marker 1290. In a different embodiment, the suture 1256 disposed within the channel 1263 can also have a coating 1296. Of note, the implant 1250 is loaded into the cannula 1235 by any method now known or later developed, including but not limited to hand loading and machine loading.

After the implant 1250 is transferred from the cannula 1235 to the body, or more specifically, the organ 1288, the implant 1250 can be secured to the human body. In one embodiment, the implant 1250 can be secured to the human body by attaching at least a portion of the suture thread 1256 of the implant 1250 to the human body. In a different embodiment, a separate piece of suture thread can be used to attach the implant 1250 to the human body (whether to tissue, a body cavity, organ, and/or a tumor). In yet a different embodiment, the implant 1250 is not physically secured, but instead the organ 1288 collapses around the implant 1250 securing the implant 1250 in place. In one embodiment, the organ 1288 can be aspirated, such as via an introducer, allowing the organ 1288 (or cavity) to collapse and conform to the size and/or shape of the implant 1250. Regardless of whether the implant 1250 is or is not separately secured to the human body, a radiation beam from an external beam radiation source 1289 can be aimed at the implant 1250. Thereafter, the external beam radiation source 1289 is activated.

Of note, in one embodiment, the implant 1250 is left in the body. In other words, the implant 1250 is not removed. However, over time, the suture thread 1256 as well as the coating 1296 are absorbed by the body, but the marker(s) 1290 are not absorbed and remain in the body. Of note, neither the cannula 1235 (shown in FIG. 12) nor a needle 1326 (shown in FIG. 13) are left in the body, but are, instead, removed.

Of further note, in use, following a lumpectomy or other procedure, an implant 1250 can be placed into the body cavity during surgery or post-operation under ultrasound guidance or other radiographic modality. After placement of the implant 1250, optionally, the body cavity can be aspirated via the introducer; for example, allowing the cavity to collapse and conform to the size and/or shape of the implant 1250. A radiation beam from an external beam radiation source 1289 can then be used to target the implant 1250 or any markers 1290 coupled to the implant 1250 so that radiation therapy can be delivered to the body at the location of the implant 1250 or markers 1290. After the completion of the radiation therapy, in one embodiment, the implant 1250 can be removed from the body under ultrasound guidance or any other radiographic modality. However, in a different, but preferred, embodiment, the implant 1250 is left in the body.

In yet even further illustration of the inventive implant, FIG. 13 illustrates implants 1350 being inserted into tissue 1388, such as breast tissue. In particular, each implant 1350 has a marker 1390 defining a channel 1363 therethrough in which a suture 1356 (or suture thread) is disposed and where both the marker 1390 and the suture 1356 are covered by a coating 1396. Of note, in one embodiment, the coating 1396 can be made from the same material as the suture 1356. The coating 1396 can further be a U.S. Food and Drug Administration (FDA) approved material. Additionally, the coating 1396 can be used to fix in place the marker 1390 on the suture 1356. In other words, the coating 1356 can act as a glue. The coating 1396 can further prevent any marker 1390 from cutting into tissue or organ as it is implanted. More specifically, the coating 1396 prevents the marker 1390 from cutting into tissue as the implant 1350 is threaded or passed through tissue upon implantation. The coating 1396 can be applied to both the entire outer surface of the marker 1390 and the suture 1356, as shown in FIG. 13, by any method now known or later developed, including but not limited to painting and dipping. Of note, the coating 1396 can also, in a different embodiment, be applied to only a portion of the outer surface of the suture 1356 and also to the entire outer surface of the marker 1390. In other words, regardless of the embodiment, the coating 1396 covers at least a portion of the suture 1356 as well as the marker 1390. Of note, in a preferred embodiment, the coating 1396 is not applied or found on the portion of the suture 1356 disposed within the channel 1363. However, in a different embodiment, a coating 1396 can also be applied to the portion of the suture 1356 disposed within the channel 1363 as well as the portion of the suture 1356 not within the channel 1363, such as when a coating is first applied to an entire suture 1356, then one or more markers 1390 is coupled to the coated suture 1356, followed by a continuous coating 1396 being applied to each marker 1390 and to at least a portion of the coated suture 1356 adjacent to and extending past both ends of each marker 1390. Further, each marker 1390 can be crimped or squeezed to the suture 1356 by a specialized tool resulting in each marker 1390 being tapered 1362 at each end. Further, in an embodiment, the suture 1356 is flexible, i.e. it can be bent by only hand strength.

In further description of the invention, the marker 1390, suture 1356, and coating 1396 (which all together form the implant 1350) are further coupled to a needle 1326 (as opposed to being placed in a cannula as shown in FIG. 12). Of note, the needle 1326 can be straight as shown in FIG. 13 or curvilinear as shown in FIG. 10A. Additionally, the needle 1326 can be attached to the implant 1350 (in particularly, to the suture 1356) by any method now known or later developed. Also, though FIG. 13 illustrates two implants 1350 positioned into tissue 1388, there can be one or more implants 1350 placed within a body cavity or tissue 1388. Additionally, although FIG. 13 illustrates each implant 1350 as including only one marker 1390, an implant 1350 can include more than one marker 1390. Further, as described above with respect to FIGS. 11 and 12, the marker 1390 can include zero or more apertures 1356 arranged randomly or in a pattern. Also, both a combination of different markers 1390, such as where one marker 1390 may have one or more apertures 1358 in one pattern, a different marker 1390 may lack apertures 1358, and yet a different marker 1390 in the same implant 1350 may have one or more randomly placed apertures 1358. Of note, in addition to the channel 1133 running from one end of the marker 1390 to the opposite end of the marker 1390 (as well as on the central horizontal axis of the marker 1390, in an embodiment), the surface of the marker 1390 can also define zero or more apertures 1358. These apertures 1358 can be added to the marker 1390 by any method now known or later developed, including etching (see FIGS. 14A and 14B), stamping, and laser cutting (see FIG. 15). Further, the marker 1350 can be both non-radioactive and also radio-opaque. Yet further, the marker 1350 can be non-absorbable by the human body.

Additionally, although the preferred embodiment includes the suture 1356 being disposed within the channel 1363 of the marker 1390, the suture 1356 does not need to be disposed within the channel 1363 in all embodiments. For example, in one embodiment, the suture 1356 can include multiple suture threads, where one end of a suture 1356 is coupled to an end of one marker 1390 and an end of a different marker 1390, such that no suture 1356 is disposed within the entire channel 1363 of the marker 1390. Regardless of whether the suture 1356 is in the channel 1363, the suture 1356 in a preferred embodiment is non-looping. In other words, no loops are formed with the suture 1356 with respect to any marker 1390 prior to implantation of the implant 1350 into a body (i.e. body cavity, tissue, or organ). In particular, the suture 1356 is not passed through the marker more than once. Also, the suture 1356 is not knotted prior to implantation. In others words, the suture 1356 is not knotted so to secure a marker 1390 in place on the implant 1350. However, after the implant 1350 is placed within a body, the suture 1356 may then be secured to the body (cavity, tissue, and/or organ) by attaching the implant to the body by looping the suture 1356 and/or tying a knot with the suture 1356.

After an implant 1350 is inserted into the tissue 1388, the implant 1350 can be secured in place by using the needle 1326 coupled to the suture 1356. More specifically, in a preferred embodiment where the implant 1350 includes a flexible or elastic-type suture 1356, a portion of that suture 1356 that forms the implant 1350 is used to secure the implant after placement into a body cavity or tissue 1388, such as breast tissue. In a different embodiment, the implant 1350 can be secured by collapsing the tissue (or body cavity) 1388 around the implant. In yet a different embodiment, the implant 1350 can be fixed in place by a different suture 1356 that is not part of the implant 1350. Of note, any implants 1350 can be first placed into the tissue 1388 before securing each implant 1350 in place or each implant 1350 can be secured directly after positioning before placement of the next implant 1350.

Once the implant 1350 is secured in place (whether physically, such as with the suture 1356 itself or by allowing tissue 1388 to collapse around the implant 1350), the needle 1326 can be removed. In one embodiment, the needle 1326 is a "pop-off" needle that separates from the implant 1350 with a slight tug after the implant is securely positioned in the body. In a different embodiment, the needle 1326 is cut from the implant 1350 after the implant 1350 is secured. Of note, it should be understood that the needle 1326 can be separated from the implant 1350 before the implant 1350 is secured. As such, in a preferred embodiment, the implant 1350 remains in the body (cavity or tissue 1388), but the needle 1326 is removed. Thereafter, an external beam radiation source can be aimed at the implant 1350 (and in particular one or more markers 1390), and then the external beam radiation source 1289 can be activated. Of further note, over time, both the suture 1356 and the coating 1396 can be absorbed by the body (i.e. dissolve), but the marker 1390 is not absorbed and remains in the body (as illustrated in FIG. 12). In a different embodiment, the implant 1350 can be removed from the body.

Figures 14A, 14B:
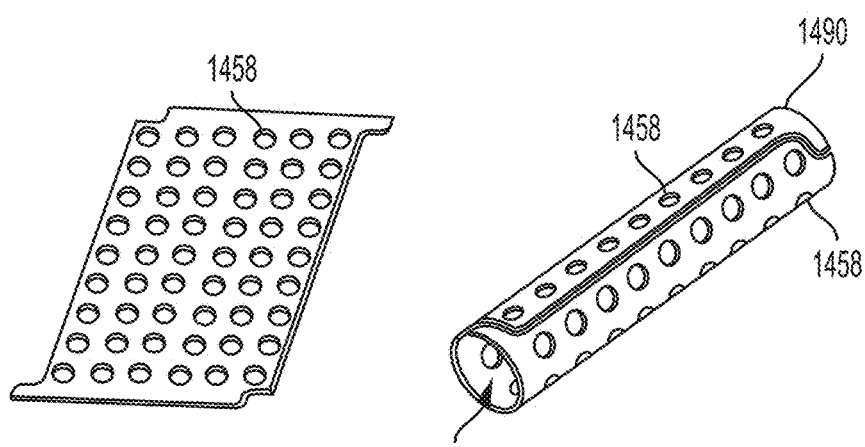
FIGS. 14A and 14B illustrate an embodiment of the making of a marker.

In further illustration of the invention, FIGS. 14A and 14B illustrate an embodiment of the making of a marker 1490. More specifically, an etching process can be used to cut away a flat pattern design from a sheet of material, such as gold, platinum iridium, or other radio-opaque material. In particular, the etching process can produce one or more holes or apertures 1458. Further, as described above, the one or more apertures 1458 can be created to form a pattern or randomly placed. After the sheet is rolled to form a marker 1490 having a channel 1463, as shown in FIG. 14B, and implanted into a body, tissue can grow inside and through the apertures 1458 and aid in securing the marker 1490 in place after a suture coupled to the marker 1490 is absorbed by the body.

Figure 15:
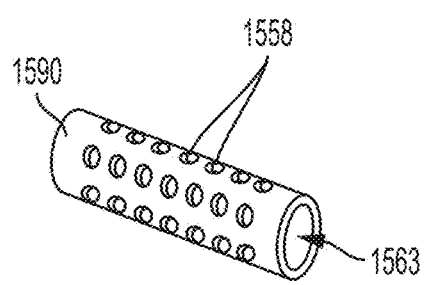
FIG. 15 illustrates a different embodiment of the making of a marker.

In yet further illustration, FIG. 15 illustrates a different embodiment for the making of a marker 1590. In particular, laser cutting by a precise machining device can be used to cut one or more cutouts or apertures 1558 from a tube-shaped piece of material, such as gold, platinum iridium, or other radio-opaque material. Further, as described herein, the one or more apertures 1558 can be created to form a pattern or randomly placed. After the marker 1558 having one or more apertures 1558 and a channel 1563 is implanted into the body, tissue can grow inside and through the one or more apertures 1558 and aid in securing the marker 1590 in place after a suture coupled to the marker 1590 is absorbed by the body.

It should be understood that the various Figures show different embodiments of various implants with various different embodiments of markers. More specifically, each implant can include a different number of markers, different markers, and/or markers of all the same design. In particular, as shown in FIG. 11, an implant 1150 can include two different markers 1190, one having apertures 1158 arranged in no particular pattern and crimped 1162 on each end and a different marker 1190 not crimped, but having apertures 1158 arranged in a pattern. But in a different embodiment, as shown in FIG. 12, a marker 1290 can have no apertures. In other words, markers are shown without apertures, with apertures in a pattern, and with apertures not in a pattern, but it should be understood that any combination of markers with or without apertures can be used. Additionally, each implant can include one or more markers that are crimped (FIG. 13), not crimped (FIG. 12), or a combination of both (FIG. 11).

Having thus described the invention of the present application in detail and by reference to embodiments thereof, it will be apparent that modifications and variations are possible without departing from the scope of the invention defined in the appended claims as follows.

We claim:

1. A radiation target, comprising:
an implant, the implant comprising:
a marker comprising a channel defined therethrough from one end of the marker to an opposite end of the marker;
a single non-looping suture thread disposed within the channel and extending past both ends of the marker; and,
a continuous coating covering the marker and extending from at least a portion of the single non-looping suture thread adjacent to one end of the marker to at least a portion of the single non-looping suture thread past the opposite end of the marker.

2. The radiation target of claim 1, wherein the marker further defines one or more apertures on a surface of the marker.

3. The radiation target of claim 1, further comprising a needle coupled to the implant.

4. The radiation target of claim 1, further comprising a cannula, wherein the implant is disposed within the cannula.

5. The radiation target of claim 1, wherein the marker is cylindrically shaped.

6. The radiation target of claim 1, wherein both the single non-looping suture thread and also the coating are absorbable and the marker is non-absorbable.

7. The radiation target of claim 1, wherein the marker is both non-radioactive and also radio-opaque.

8. The radiation target of claim 1, wherein the marker is made from a metal.

9. The radiation target of claim 1, wherein the marker is made from ceramic.

10. The radiation target of claim 1, wherein the channel is located on a central longitudinal axis passing through the marker.

11. The radiation target of claim 1, wherein a portion of each end of the marker is crimped to the single non-looping suture thread.

12. The radiation target of claim 1, wherein the implant comprises two or more markers, wherein each marker has a channel defined therethrough from one end of each marker to an opposite end of each marker, and wherein the single non-looping suture thread is disposed within each channel of each marker and extends past both ends of each marker.

13. The radiation target of claim 1, wherein the continuous coating further covers the entirety of an outer surface of the single non-looping suture thread.

* * * * *